US009119685B2

(12) United States Patent
Butler et al.

(10) Patent No.: US 9,119,685 B2
(45) Date of Patent: Sep. 1, 2015

(54) SURGICAL INSTRUMENT AND METHOD

(71) Applicant: Warsaw Orthopedic, Inc., Warsaw, IN (US)

(72) Inventors: Brian Butler, Atoka, TN (US); Jason May, Cordova, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 121 days.

(21) Appl. No.: 13/646,990

(22) Filed: Oct. 8, 2012

(65) Prior Publication Data

US 2014/0100583 A1    Apr. 10, 2014

(51) Int. Cl.
*A61B 17/56* (2006.01)
*A61B 17/88* (2006.01)
*A61B 17/70* (2006.01)
*A61F 2/46* (2006.01)
*A61B 17/00* (2006.01)

(52) U.S. Cl.
CPC ......... *A61B 17/8875* (2013.01); *A61B 17/7082* (2013.01); *A61B 17/888* (2013.01); *A61B 17/8872* (2013.01); *A61B 2017/0046* (2013.01); *A61F 2/4611* (2013.01)

(58) Field of Classification Search
CPC ........... A61B 17/7082; A61B 17/8875; A61B 17/888; A61B 2017/0046; A61F 2/4611
USPC .................... 81/451–458; 606/86 A, 99, 104
See application file for complete search history.

(56) References Cited

U.S. PATENT DOCUMENTS

| | | | |
|---|---|---|---|
| 3,351,054 A | 11/1967 | Florek | |
| 4,429,938 A | 2/1984 | Flor | |
| 4,842,439 A | 6/1989 | Caldwell et al. | |
| 5,096,213 A | 3/1992 | Terwilliger et al. | |
| 5,405,404 A | 4/1995 | Gardner et al. | |
| 5,439,005 A | 8/1995 | Vaughn | |
| 5,476,467 A | 12/1995 | Benoist | |
| 5,867,912 A * | 2/1999 | Hickok et al. | 30/329 |
| 5,941,891 A | 8/1999 | Walen | |
| 6,328,494 B1 * | 12/2001 | Moxon | 401/8 |
| 7,559,927 B2 | 7/2009 | Shores et al. | |
| 7,651,502 B2 * | 1/2010 | Jackson | 606/99 |
| D625,803 S | 10/2010 | Studenec | |
| 2003/0229351 A1 | 12/2003 | Tidwell et al. | |

* cited by examiner

*Primary Examiner* — Anu Ramana
(74) *Attorney, Agent, or Firm* — Sorell Lenna & Schmidt LLP

(57) ABSTRACT

A surgical instrument includes a first member extending between a proximal end and a distal end. The distal end includes a plurality of fingers extending radially outward in a tapered configuration. A second member extends between a proximal end and a distal end. The proximal end of the second member is configured for mating with the distal end of the first member. A third member has an inner surface defining a cavity configured for disposal of the first member and engagement with the first member to fix the first member with the second member. Systems and methods are disclosed.

18 Claims, 4 Drawing Sheets

SURGICAL INSTRUMENT AND METHOD

TECHNICAL FIELD

The present disclosure generally relates to medical devices for the treatment of musculoskeletal disorders, and more particularly to a surgical system for delivering and/or fastening implants with a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attaching rods and plates to the exterior of two or more vertebral members. This disclosure describes an improvement over these prior art technologies.

SUMMARY

In one embodiment, in accordance with the principles of the present disclosure, a surgical instrument is provided. The surgical instrument includes a first member extending between a proximal end and a distal end. The distal end includes a plurality of fingers extending radially outward in a tapered configuration. A second member extends between a proximal end and a distal end. The proximal end of the second member is configured for mating with the distal end of the first member. A third member has an inner surface defining a cavity configured for disposal of the first member and engagement with the first member to fix the first member with the second member.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
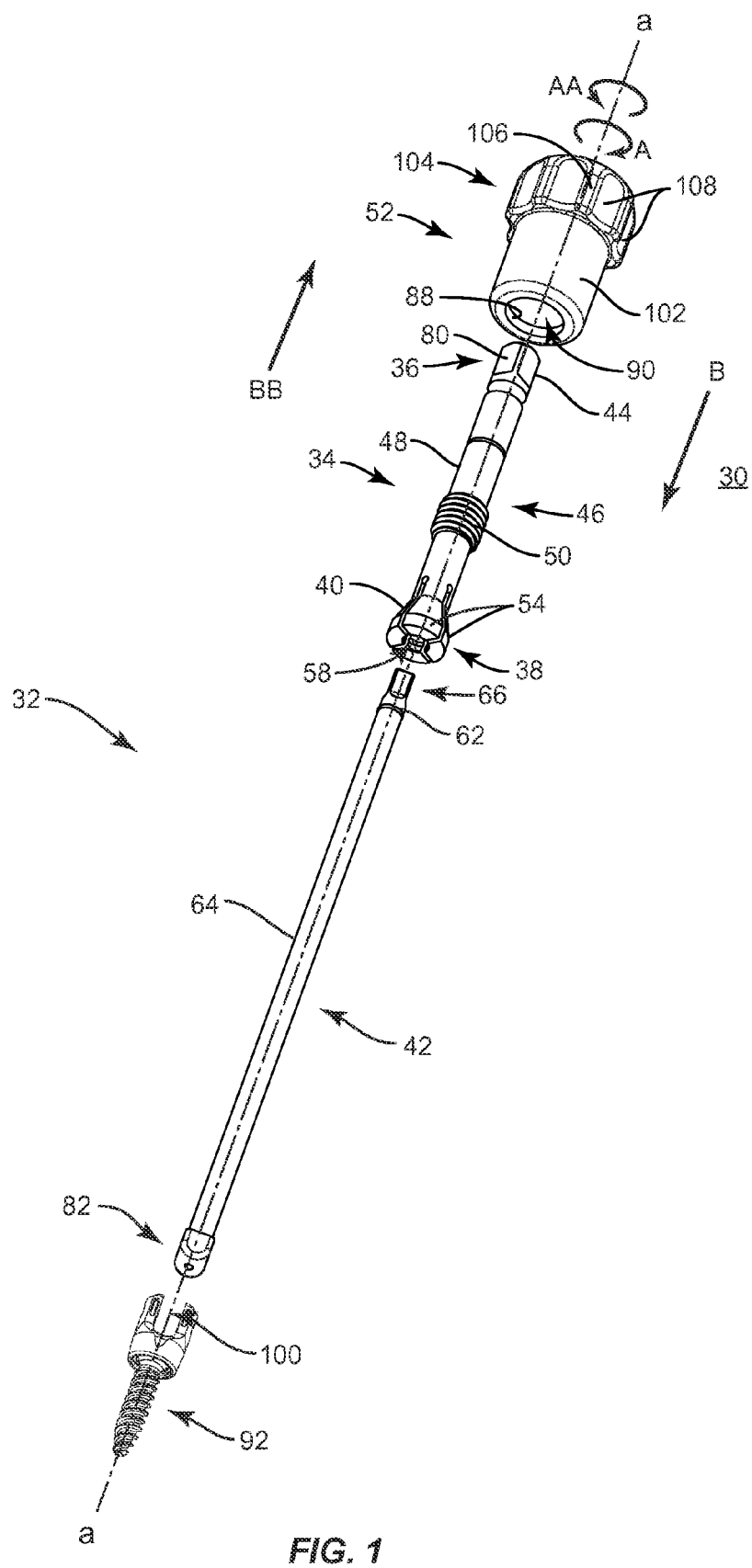
FIG. 1 is a perspective view of one particular embodiment of components of a surgical implant system in accordance with the principles of the present disclosure with parts separated.

The exemplary embodiments of a surgical system are discussed in terms of medical devices for the treatment of musculoskeletal disorders and more particularly, in terms of a surgical implant system for delivering and/or fastening implants with a surgical site and a method for treating a spine. In one embodiment, the system includes a surgical instrument including a first shaft defining a female end of a collet configuration and a second shaft defining a male end of the collet configuration. The shafts have mating geometries that provisionally lock the shafts together to prevent rotation and axial movement of the second shaft relative to the first shaft. A third member is tightened on the female end of the collet such that the male end of the collet engages the female end to lock the first shaft to the second shaft.

In one embodiment, the system includes a surgical instrument capable of disassembly to facilitate cleaning of each of the components of the surgical instrument. This configuration provides access to areas of the surgical instrument, including difficult to reach areas and/or inaccessible areas due to a surgical instrument's assembled configuration. It is envisioned that the surgical instrument is capable of disassembly and assembly. In one embodiment, the surgical instrument includes a collet style connection mechanism to facilitate disassembly and assembly. It is contemplated that the surgical instrument may be disassembled and assembled without additional tools or other instruments.

It is envisioned that the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the system of the present disclosure may be employed with other osteal and bone related applications, including those associated with diagnostics and therapeutics. It is further contemplated that the disclosed system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there is illustrated components of a surgical implant system 30 including a surgical instrument, such as, for example, a surgical driver 32, in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference. The components of system 30, individually or collectively, may also be fabricated from a heterogeneous material such as a combination of two or more of the above-described materials. The components of system 30 may be monolithically formed, integrally connected or include fastening elements and/or instruments, as described herein.

System 30 is employed, for example, with an open or mini-open, minimal access and/or minimally invasive including percutaneous surgical technique to deliver and fasten an implant, such as, for example, a bone fastener at a surgical site within a body of a patient, for example, a section of a spine. In one embodiment, the components of system 30 are configured to fix a spinal rod, connector and/or plate to a spine via a bone fastener for a surgical treatment to treat various spine pathologies, such as those described herein.

Driver 32 includes a first member, such as, for example, a collet 34 that defines a longitudinal axis a. Collet 34 extends between a proximal end 36 and a distal end 38. End 38 defines an engagement portion 40 configured to removably engage a second member, such as, for example, a shaft 42. Shaft 42 and collet 34 are provisionally lockable to prevent axial translation of shaft 42 relative to collet 34 along axis a. End 36 defines a drive portion 44 configured to engage an instrument, such as, for example, a socket tool or a wrench. Driver 32 is configured to rotate collet 34 about axis a in the direction shown by arrow A and the direction shown by arrow AA.

Collet 34 includes an intermediate portion 46 positioned between ends 36, 38 having an outer surface 48 including a first thread form 50 configured to engage a thread form of a third member, such as, for example, a handle 52. Handle 52 engages portion 40 to lock shaft 42 with collet 34 to prevent rotation of shaft 42 relative to collet 34 about axis a. It is envisioned that collet 34 may be disposed with handle 52 in alternate fixation configurations, such as, for example, friction fit, pressure fit, locking protrusion/recess, locking keyway and/or adhesive. It is contemplated that all or only a portion of surface 48 and/or handle 52 may have alternate surface configurations to enhance engagement with one another such as, for example, rough, arcuate, undulating, mesh, porous, semi-porous, dimpled and/or textured, according to the requirements of a particular application.

Portion 40 includes a plurality of cantilevered fingers 54 extending radially outward from surface 48. Fingers 54 are circumferentially disposed about end 38 and are equidistantly spaced apart. Fingers 54 are spaced apart by a gap 68 defined by opposite planar sidewalls 70. Sidewalls 70 converge at an arcuate portion 72 configured to allow fingers 54 to move or deflect. Fingers 54 move such that a width of each gap 68 defined by a distance between sidewalls 70 may increase and decrease. In one embodiment, portion 40 includes four fingers 54. It is contemplated that portion 40 may include at least two fingers 54. It is envisioned that fingers 54 may be variously configured and oriented along portion 40, such as, staggered, consistent or variable, depending on the requirements of a particular application. It is further envisioned that all or a portion of gaps 68, including sidewalls 70 and portion 72 may be variously configured and dimensioned such as, for example, planar, concave, convex, polygonal, irregular, uniform, non-uniform, staggered, tapered, consistent or variable, depending on the requirements of a particular application.

Figure 5:
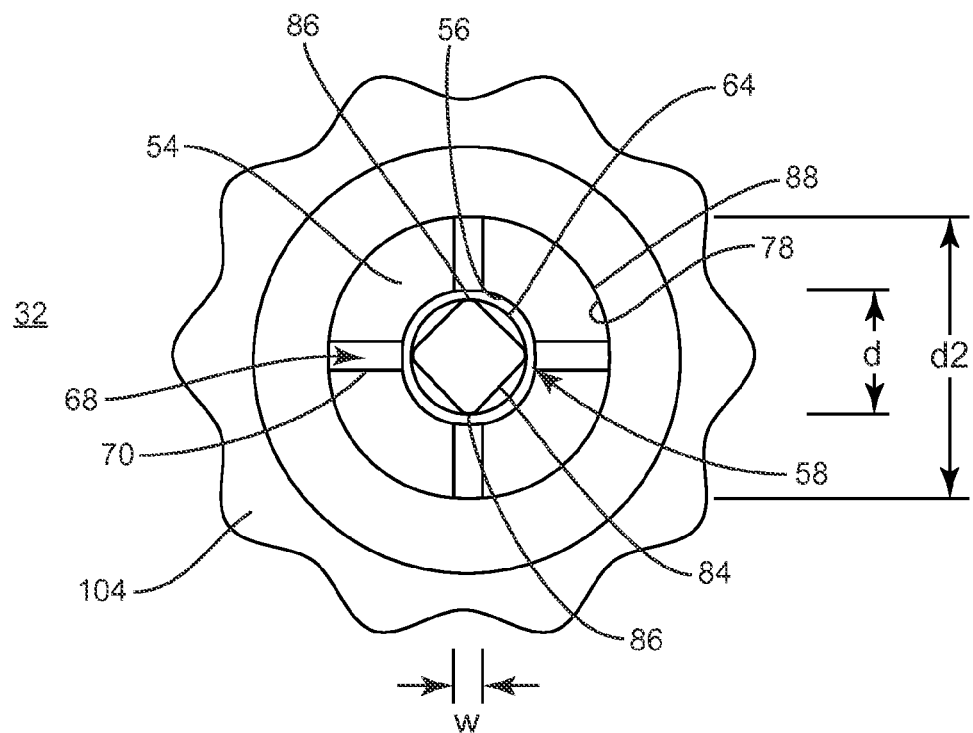
FIG. 5 is a cross section view of components of the spinal implant system shown in FIG. 1.
Figure 6:
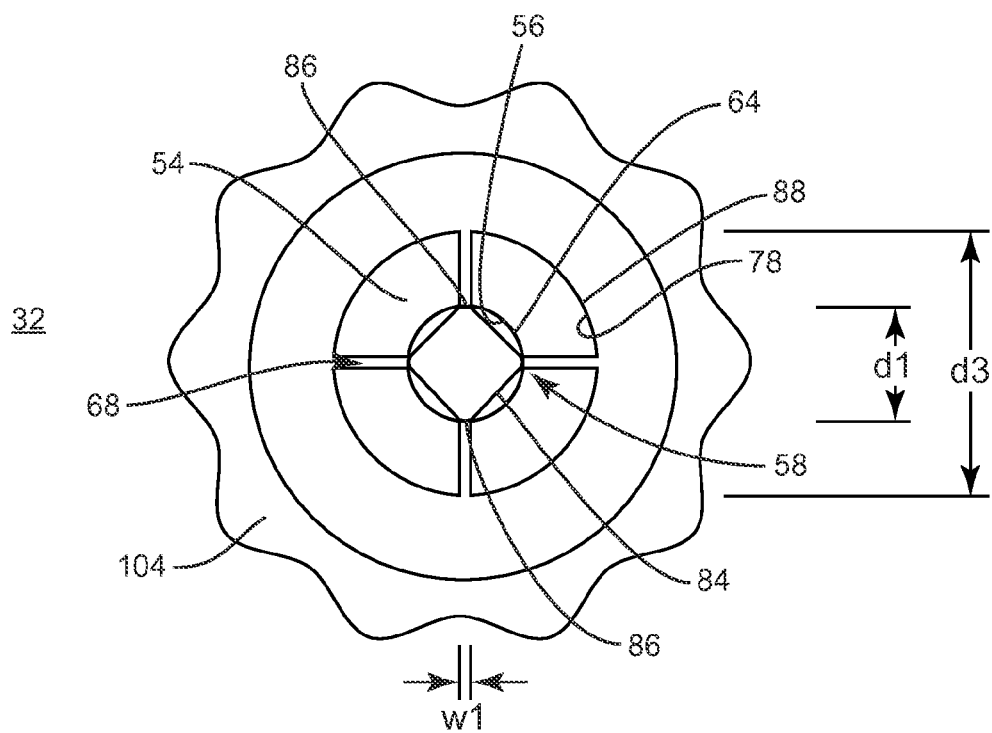
FIG. 6 is a cross sectional view of components of the spinal implant system shown in FIG. 1.

In one embodiment, fingers 54 are movable between a first, expanded configuration, as shown in FIG. 5, and a second, contracted configuration, as shown in FIG. 6. In a first configuration, gaps 68 have a width w between sidewalls 70. As fingers 54 move to a second configuration, gaps 68 have a width w1 between sidewalls 70 that is less than width w. The overall diameter of portion 40 decreases when fingers 54 move from a first configuration to a second configuration.

In a first configuration of fingers 54, a proximal end 66 of shaft 42 is capable of axial translation along axis a and rotation about axis a. In a second configuration of fingers 54, end 66 is fixed with surface 56, as will be described herein. In a second configuration, shaft 42 is prevented from rotating relative to collet 34 about axis a in the direction shown by arrow A or the direction shown by arrow AA. In a second configuration, shaft 42 is prevented from translating axially relative to collet 34 along axis a in the direction shown by arrow B or the direction shown by arrow BB.

Fingers 54 each include an inner surface 56 that defines a cavity, such as, for example, a socket 58 in portion 40. Socket 58 has a cylindrical cross sectional configuration for disposal of shaft 42. In a first configuration of fingers 54, socket 58 has a diameter d. In a second configuration of fingers 54, socket 58 has a diameter d1 that is less than diameter d. Shaft 42 has a cylindrical cross sectional configuration including a diameter that is less than diameter d1.

In a first configuration of fingers 54, surface 56 is spaced apart from shaft 42, as shown in FIG. 5. In a first configuration, shaft 42 is axially translatable along axis a within socket 58, in the direction shown by arrow B or the direction shown by arrow BB. In a second configuration of fingers 54, surface 56 engages shaft 42 to lock shaft 42 and collet 34, as shown in FIG. 6. In a second configuration, shaft 42 is prevented from translating axially along axis a within socket 58 and/or rotating about axis a. It is envisioned that all or only a portion of socket 58 and/or shaft 42 may have alternate cross section configurations, such as, for example, oval, oblong triangular, square, polygonal, irregular, uniform, non-uniform, offset, staggered, and/or tapered, depending upon the requirements of a particular application.

Surface 56 is substantially smooth or even. Surface 56 includes a concave groove 60 extending transverse to axis a across fingers 54. Shaft 42 includes a convex ridge 62 extending transversely to axis a across a smooth or even outer surface 64 of end 66. Ridge 62 projects outwardly from surface 64. Ridge 62 is configured for disposal in groove 60 when shaft 42 engages collet 34 and fingers 54 are disposed in a first configuration to provisionally lock shaft 42 and collet 34 to one another. Ridge 62 engages groove 60 to provisionally lock shaft 42 with collet 34. This configuration prevents shaft 42 from translating axially along axis a within socket 58. In a second configuration of fingers 54, ridge 62 maintains engagement with groove 60. Surface 56 engages surface 64 to prevent shaft 42 from translating axially along axis a within socket 58 and/or rotating about axis a.

It is envisioned that all or only a portion of surface 56 and/or surface 64 may have alternate surface configurations to enhance engagement with one another such as, for example, rough, arcuate, undulating, mesh, porous, semi-porous, dimpled and/or textured, according to the requirements of a particular application. It is further envisioned that all or only a portion of groove 60 and/or ridge 62 may be variously configured and dimensioned, such as, for example, planar, concave, convex, polygonal, irregular, uniform, non-uniform, staggered, tapered, consistent or variable, depending on the requirements of a particular application. It is contemplated that groove 60 and/or ridge 62 may be disposed at alternate orientations, relative to axis a, such as, for example, transverse, perpendicular and/or other angular orientations such as acute or obtuse, coaxial and/or may be offset or staggered, according to the requirements of a particular application.

Portion 40 includes an outer surface having a first portion 74 extending from portion 48, a second portion 76 extending from portion 74 and a third portion 78 extending from portion 76. Portions 74, 78 extend parallel to axis a and portion 76 extends at an acute angle relative to axis a. Portion 74 has a first diameter and portion 78 has a second diameter that is greater than the first diameter. Portion 74 is tapered between a first end adjacent portion 74 and a second end adjacent portion 78. Fingers 54 taper in a proximal to distal direction such that portion 40 has a conical configuration. When fingers 54 are in a first configuration, portion 40 has a diameter d2 defined by a distance between opposite portions 78. When fingers 54 are in a second configuration, portion 40 has a diameter d3 that is less than diameter d2. Portion 76 has a minimum diameter that is substantially equivalent to the first diameter when fingers 54 are in both first and second configurations. Portion 76 has a maximum diameter that is substantially equivalent to diameter d2 when fingers 54 are in a first configuration. Portion 76 has a maximum diameter that is substantially equivalent to diameter d3 when fingers 54 are in a second configuration. It is envisioned that portions 72, 74, 76 may be disposed through angular ranges in various orientations relative to axis a, such as, for example, transverse or perpendicular and/or other angular orientations such as acute or obtuse, and/or may be offset or staggered.

Portion 44 includes an outer surface including a plurality of planar surfaces 80 extending parallel to axis a configured to engage a tool, such as, for example, a socket driver or a wrench. The tool rotates collet 34 about axis a. In one embodiment, portion 44 has a hexagonal cross sectional configuration configured for engagement with a hex socket tool or a wrench. It is envisioned that portion 44 may include one or a plurality of surfaces 80. It is further envisioned that portion 44 may include a square, hexagonal, polygonal, star or hexalobe cross sectional configuration configured to be received in a correspondingly shaped portion of a socket tool or a wrench. It is contemplated that surfaces 80 may be disposed through angular ranges in various orientations relative to axis a, such as, for example, transverse or perpendicular and/or other angular orientations such as acute or obtuse, and/or may be offset or staggered.

Portion 46 has a substantially cylindrical configuration. Surface 48 is even or smooth between thread form 50 and portion 40. Surface 48 is even or smooth between thread form 50 and portion 44. It is envisioned that thread form 50 may extend between portion 40 and portion 44 such that collet 34 is threaded along substantially the entire length of collet 34. Surface 48 has a uniform diameter between thread form 50 and portion 40. Surface 48 has a uniform diameter between thread form 50 and portion 44. Thread form 50 has a major diameter that is greater than the diameter of surface 48 between thread form 50 and portion 40. Thread form 50 has a major diameter that is greater than the diameter of surface 48 between thread form 50 and portion 44. Thread form 50 has a minor diameter that is substantially equivalent to the diameter of surface 48 between thread form 50 and portion 40. Thread form 50 has a minor diameter that is substantially equivalent to the diameter of surface 48 between thread form 50 and portion 44. It is envisioned that all or only a portion of portion 44 may be variously configured and dimensioned, such as, for example, planar, concave, convex, polygonal, irregular, uniform, non-uniform, staggered, tapered, consistent or variable, depending on the requirements of a particular application.

Shaft 42 includes a substantially cylindrical configuration between end 62 and a distal end 82. The portion of shaft 42 between end 62 and a distal end 82 is configured to engage an implant, such as, for example, a bone fastener. End 62 includes a plurality of planar surfaces 84 defining a bit or drive configuration. End 62 is configured for disposal in socket 58. When end 62 is disposed in socket 58, surfaces 84 releasably engage fingers 54 to prevent rotation of shaft 42 relative to collet 34. In one embodiment, end 62 includes four surfaces 84 each oriented perpendicular to an adjacent surface 84. End 62 includes walls 86 extending between adjacent surfaces 84 such that end 62 has a substantially diamond-shaped configuration. It is envisioned that end 62 may include one or a plurality of surfaces 84 and/or walls 86. It is further envisioned that all or only a portion of end 62 may be variously configured and dimensioned, such as, for example, circular, oval, oblong, triangular, square, rectangular, polygonal, or irregular, depending on the requirements of a particular application. It is contemplated that the bit configuration of end 62 may be variously configured and dimensioned, for example, end 62 may include a cruciform, Phillips, square, hexagonal, polygonal, star or hexalobe cross sectional configuration.

End 82 defines an implant engagement portion. The implant engagement portion is configured to releasably engage an implant, such as, for example, a bone fastener. It is contemplated that the implant may include a spinal rod, nail, staple, hook, rod, plate or intervertebral spacer. End 82 is operable to engage an implant, for example, a bone fastener, while driver 32 is rotated about axis a in the direction shown by arrow A. As driver 32 is rotated about axis a, the bone fastener also rotates about axis a in the direction shown by arrow A to fix the implant in a portion of a patient's anatomy selected by a medical practitioner such as, for example, a vertebral surface. End 82 is configured to disengage the implant following fixation of the implant with the patient. After end 82 disengages the implant, driver 32 may be withdrawn from the patient.

In one embodiment, system 30 includes a bone fastener 92 including a proximal member 94 and a distal member 94 having a threaded outer surface configured to penetrate tissue, such as, for example, bone. Member 94 includes a pair of spaced apart arms 98. Arms 98 define a U-shaped cavity 100 therebetween configured for disposal of a spinal construct, such as, for example, a spinal rod. End 82 has a U-shaped configuration configured for disposal in cavity 100. When end 82 is disposed in cavity 100, an outer surface of end 82 engages an inner surface of arms 98 defining cavity 100. It is envisioned that that all or only a portion of cavity 100 may have alternate cross section configurations, such as, for example, V-shaped, W-shaped, oval, oblong triangular, square, polygonal, irregular, uniform, non-uniform, offset, staggered, and/or tapered, depending upon the requirements of a particular application. It is further envisioned that end 82 may also have alternate cross section configurations, such as, for example, V-shaped, W-shaped, oval, oblong triangular, square, polygonal, irregular, uniform, non-uniform, offset, staggered, and/or tapered, corresponding to the configuration of cavity 100 such that the outer surface of end 82 engages the inner surface of arms 98 defining cavity 100. It is contemplated that fastener 92 may include a mono-axial screw or multi-axial screw, depending upon the requirements of a particular application.

Handle 52 includes an inner surface 88 defining a cavity 90 extending through proximal and distal ends of handle 52. Cavity 90 is configured for disposal of collet 34. Cavity 90 has a substantially cylindrical cross sectional configuration. Cavity 90 has a uniform diameter along the length thereof that is less than diameter d2 and greater than diameter d1. When collet 34 is inserted proximally into cavity 90 leading with portion 44, collet 34 translates proximally along axis a through cavity 90. As collet 34 translates proximally along axis a, portion 74 passes through cavity 90 without engaging surface 88. As collet 34 continues to translate proximally along axis a, surface 88 engages portion 76 causing fingers 54 move from a first configuration to a second configuration.

Surface 88 includes a second thread form (not shown) configured to engage thread form 50 to fix handle 52 to collet 34. In one embodiment, the second thread form extends the entire length of cavity 90. In one embodiment, the second thread form extends along a portion of cavity 90 between the proximal and distal ends of handle 52 that is less than the entire length of cavity 90. It is envisioned that surface 88 may include a plurality of thread forms, each being spaced apart from one another. It is further envisioned that handle 52 may be disposed with collet 34 in alternate fixation configurations, such as, for example, friction fit, pressure fit, locking protrusion/recess, locking keyway and/or adhesive. It is contemplated that all or only a portion surface 48 and/or surface 88 may have alternate surface configurations to enhance engagement with one another such as, for example, rough, arcuate, undulating, mesh, porous, semi-porous, dimpled and/or textured, according to the requirements of a particular application.

Handle 52 may be rotated about axis a in the direction shown by arrow A such that the second thread form on surface 88 engages thread form 50. As the second thread form on surface 88 engages thread form 50, handle 52 translates along axis a in the direction shown by arrow B. As handle 52 moves relative to collet 34 in the direction shown by arrow B, surface 88 engages portion 76, as discussed above, such that fingers 54 move from a first configuration to a second configuration. When the second thread form engages thread form 50, end 36 extends through the distal end of handle 52. When end 36 extends through the distal end of handle 52, portion 44 is accessible for engagement with an instrument. The instrument may be used to rotate collet 34 about axis a in the direction shown by arrow A or the direction shown by arrow AA. Rotating handle 52 about axis a in the direction shown by arrow AA causes handle 52 to translate along axis a in the direction shown by arrow BB. Handle 52 may be rotated about axis a in the direction shown by arrow AA to adjust the position of handle 52 relative to collet 34 and/or move fingers 54 from a second configuration to a first configuration.

Handle 52 includes an arcuate outer surface 102. Handle 52 includes uniform diameter such that handle 52 has a substantially cylindrical configuration. It is envisioned that all or only a portion of handle 52 may have alternate cross section configurations, such as, for example, oval, oblong triangular, square, polygonal, irregular, uniform, non-uniform, offset, staggered, and/or tapered, depending upon the requirements of a particular application. In one embodiment, handle 52 includes a gripping portion 104. Portion 104 has a diameter that is greater than the diameter of surface 102. Surface 102 and portion 104 are disposed in a serial configuration along axis a. Portion 104 includes a gripping surface 106 defined by a plurality of spaced apart recesses 108. Recesses 108 extend parallel to axis a. Recesses 108 are configured to facilitate gripping of handle 52 by a medical practitioner to rotate handle 52 about axis a in the direction shown by arrow A or arrow AA. It is envisioned that handle 52 may include one or a plurality of recesses 108. It is further envisioned that recesses 108 may be disposed through angular ranges in various orientations relative to axis a, such as, for example, transverse or perpendicular and/or other angular orientations such as acute or obtuse, and/or may be offset or staggered.

In assembly, operation and use, a surgical implant system, similar to system 30 described herein, is employed with a surgical procedure for treatment of a spinal disorder affecting a section of a spine of a patient, as discussed herein. For example, system 30 can be used with a surgical procedure for treatment of a condition or injury of an affected section of the spine including vertebrae (not shown). It is contemplated that one or all of the components of system 30 can be delivered or implanted as a pre-assembled device or can be assembled in situ. System 30 may be completely or partially revised, removed or replaced.

For example, spinal implant system 30 can be employed with a surgical treatment of an applicable condition or injury of an affected section of a spinal column and adjacent areas within a body, such as, for example, vertebrae. It is envisioned that system 30 may be employed with one or a plurality of vertebra. To treat a selected section of the vertebrae, a medical practitioner obtains access to a surgical site including the vertebrae in any appropriate manner, such as through incision and retraction of tissues. It is envisioned that system 30 can be used in any existing surgical method or technique including open surgery, mini-open surgery, minimally invasive surgery and percutaneous surgical implantation, whereby the vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of implantable components of system 30. A preparation instrument (not shown) can be employed to prepare tissue surfaces of vertebrae, as well as for aspiration and irrigation of a surgical region according to the requirements of a particular surgical application.

A pilot hole or the like is made in selected vertebra of the vertebrae for receiving an implant, such as, for example, fastener 92. System 30 is disposed adjacent the vertebrae at a surgical site. The components of system 30 including driver 32, are manipulable to drive, torque, insert or otherwise connect fastener 92 with the vertebrae, according to the particular requirements of the surgical treatment. For example, end 66 is inserted into socket 58 when fingers 54 are in the first configuration. Surface 56 is spaced apart from shaft 42. Shaft 42 is capable of axial translation along axis a within socket 58, as described. Shaft 42 is translated axially along axis a until ridge 62 engages groove 60 to provisionally lock collet 34 and shaft 42. Shaft 42 is prevented from translating axially along axis a. End 66 is rotated about axis a until walls 86 are aligned with gaps 68, as shown in FIG. 5.

Portion 44 is inserted within cavity 90 to engage handle 52 with collet 34. Collet 34 is advanced along axis a in the direction shown by arrow BB within cavity 90. Collet 34 is advanced along axis a until thread form 50 is aligned with the second thread form and portion 74 passes through cavity 90. Once portion 74 passes through cavity 90, portion 44 is accessible for engagement with an instrument. The instrument may rotate collet 34 about axis a. Handle 52 is rotated in the direction shown by arrow A such that handle 52 translates axially relative to collet 34 along axis a in the direction shown by arrow B. Handle 52 is rotated until handle 52 translates axially such that surface 88 engages portion 76. As surface 88 engages portion 76, fingers 54 move from a first configuration to a second configuration.

Figure 2:
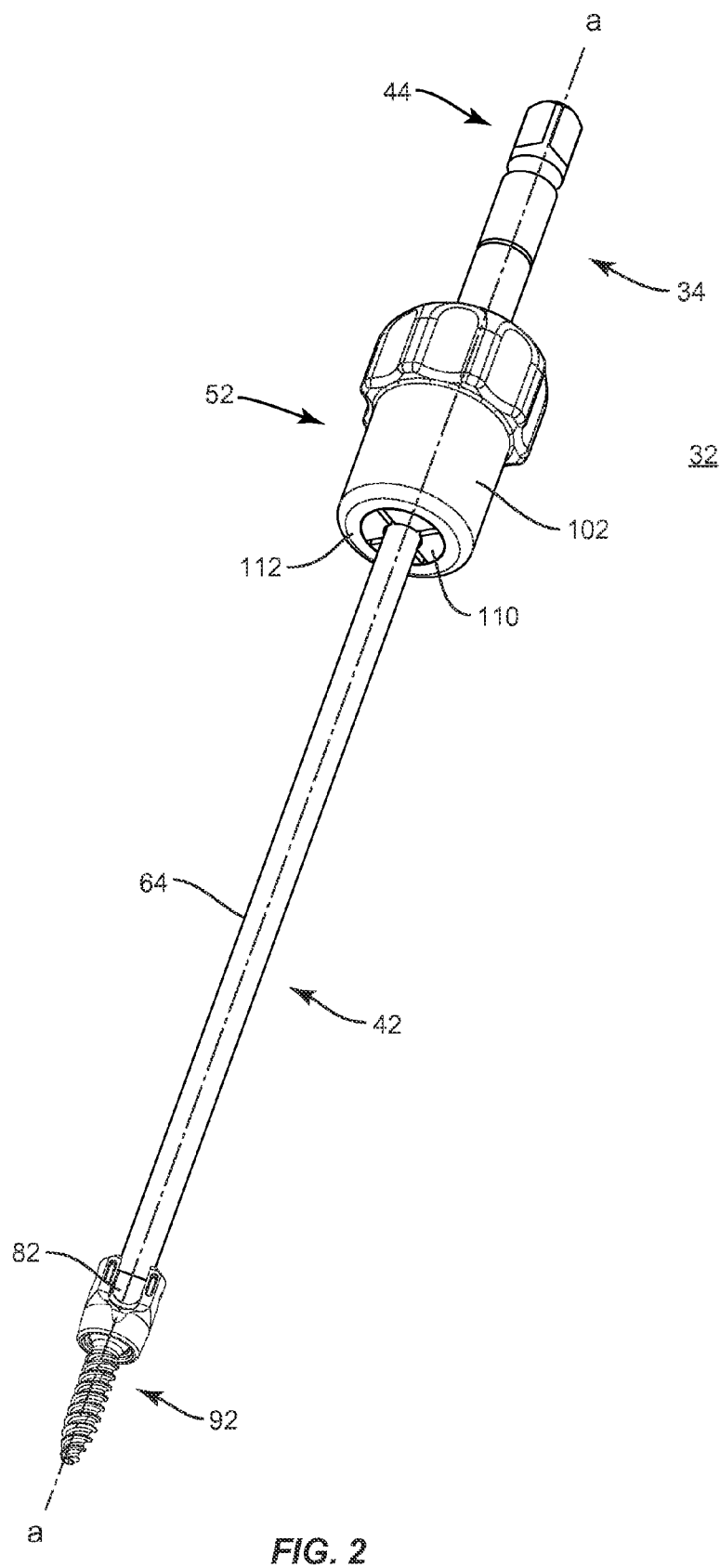
FIG. 2 is a perspective view of the surgical implant system shown in FIG. 1.
Figure 3:
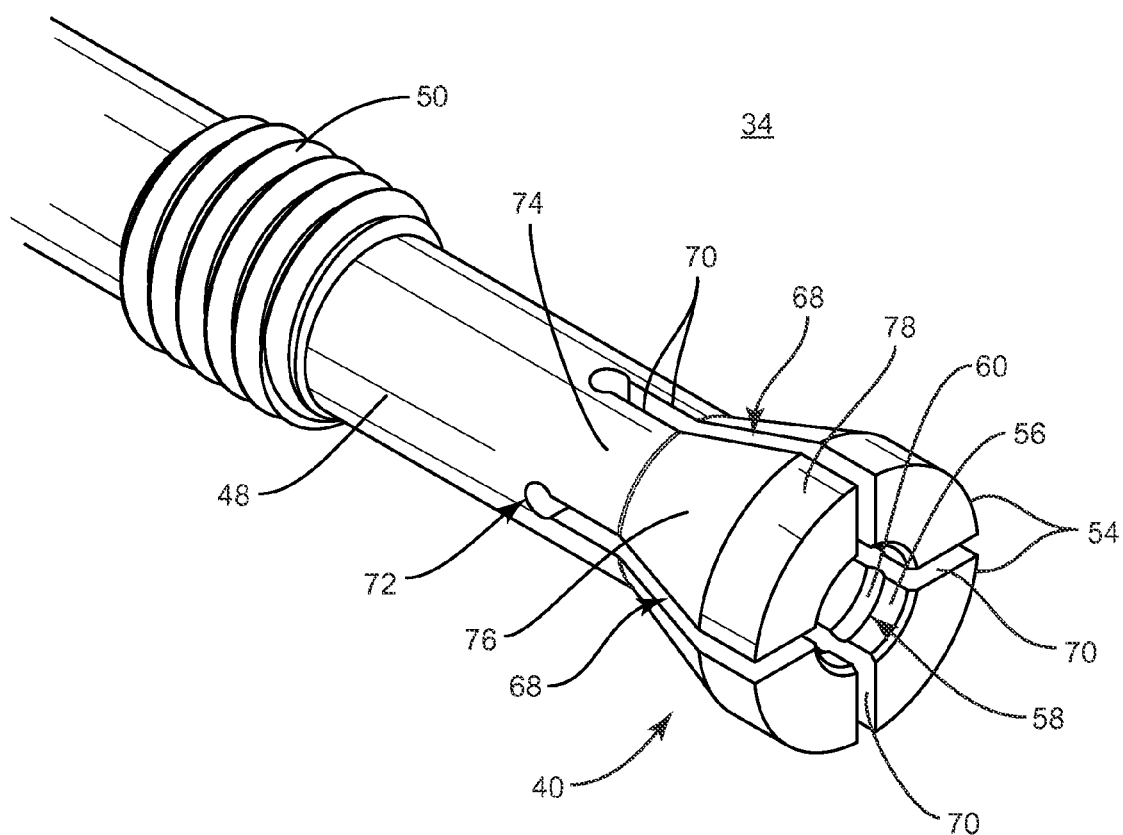
FIG. 3 is a break away perspective view of a component of the surgical implant system shown in FIG. 1.
Figure 4:
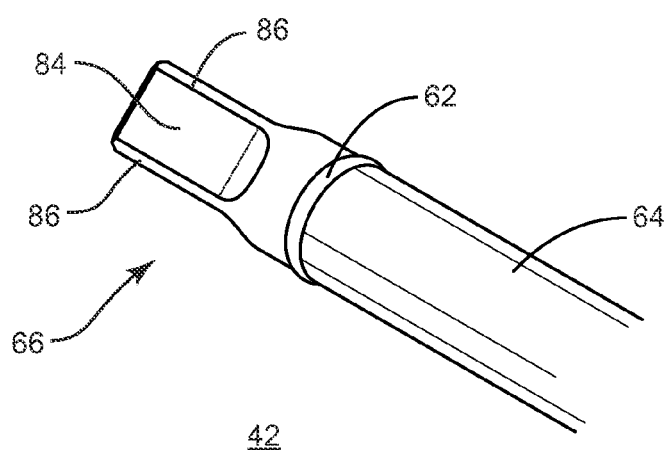
FIG. 4 is a break away perspective view of a component of the surgical implant system shown in FIG. 1.

Handle 52 may translated axially along axis a in the direction shown by arrow B until a distal face 110 of fingers 54 is flush with a distal face 112 of handle 52, as shown in FIG. 2. When fingers 54 are in the second configuration, surface 56 engages shaft 42 to lock shaft 42 and collet 34, as shown in FIG. 6, such that shaft 42 is prevented from translating axially along axis a within socket 58 and/or rotating about axis a. Fingers 54 engage end 66 in a driving interface configuration to provide a driving torque to rotate shaft 42 about axis a as collet 34 is rotated about axis a. When fingers 54 are in the second configuration, walls 86 are disposed within gaps 68, as shown in FIG. 6. In one embodiment, walls 86 engage sidewalls 70 when fingers 54 are in the second configuration.

End 82 is inserted into cavity 100 such that the outer surface of end 82 engages the inner surfaces of arms 98 defining cavity 100 to matingly and releasably fix driver 32 with fastener 92. End 82 engages the inner surfaces of arms 98 in a driving interface configuration to provide a driving torque to rotate fastener 92 about axis a when shaft is rotated about axis a to fix fastener 92 with the vertebrae. Fastener 92 is positioned in the pilot hole such that threads on member 96 engage tissue adjacent the pilot hole. An instrument, such as, for example, a socket tool or a wrench engages portion 44 to rotate collet 34 about axis a in the direction shown by arrow A. Rotating collet 34 about axis a in the direction shown by arrow A also causes shaft 42 and fastener 92 to rotate about axis a in the direction shown by arrow A. Collet 34 is rotated about axis a in the direction shown by arrow A such that fastener 92 translates axially along axis a in the direction shown by arrow B. Collet 34 may be rotated about axis a until fastener 92 is positioned at a desired depth in the vertebra, according to the preference of the medical practitioner. The depth of fastener 92 in the vertebra may be adjusted by rotating collet 34 in the direction shown by arrow AA such that fastener translates axially along axis a within the vertebra in the direction shown by arrow BB.

Once access to the surgical site is obtained, the particular surgical procedure is performed. The components of system 30, including driver 32 and fastener 92 are employed to augment the surgical treatment. For example, fastener 92 may be inserted into bone or other tissue with driver 32, for example via clockwise or counterclockwise rotation. Fastener 92 may be delivered, introduced, inserted and/or removed from the bone or other tissue with driver 32. Upon completion of a surgical procedure, driver 32 may be disengaged from fastener 92, and the non-implanted components, including driver 32 may be removed from the surgical site and the incision closed.

In one embodiment, driver 32 is disassembled, as described herein, to facilitate cleaning of one or all of the components of driver 32. The configuration of the collet connection mechanism of driver 32 provides access to areas of driver 32, including difficult to reach areas and/or inaccessible areas due to its assembled configuration. Driver 32 may be re-assembled for use in a surgical procedure. It is envisioned that system 30 may comprise various instruments including the collet connection configuration of the present disclosure, such as, for example, inserters, extenders, reducers, spreaders, distractors, blades, retractors, clamps, forceps, elevators and drills, which may be alternately sized and dimensioned, and arranged as a kit, according to the requirements of a particular application It is contemplated one or a plurality of bone fasteners may be employed with a single vertebral level. It is further contemplated that the bone fasteners may be engaged with vertebrae in various orientations, such as, for example, series, parallel, offset, staggered and/or alternate vertebral levels. System 30 can be used with various bone fasteners, mono-axial screws, pedicle screws or multi-axial screws used in spinal surgery.

In one embodiment, system 30 includes an agent, which may be disposed, packed or layered within, on or about the components and/or surfaces of system 30. It is envisioned that the agent may include bone growth promoting material, such as, for example, bone graft to enhance fixation of the bone fasteners with the vertebrae. It is contemplated that the agent may include one or a plurality of therapeutic agents and/or pharmacological agents for release, including sustained release, to treat, for example, pain, inflammation and degeneration. The components of system 30 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of system 30.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a monolithic first member extending between a proximal end and a distal end, the distal end including a plurality of fingers extending radially outward in a tapered configuration, the fingers each including an inner surface such that the inner surfaces of the fingers jointly define a socket;
   a second member extending between a proximal end and a distal end, the proximal end of the second member having a bit configuration defined by a plurality of substantially planar side surfaces, the proximal end of the second member being configured to be received within in the socket such that the side surfaces engage the inner surfaces to prevent rotation of the second member relative to the first member; and
   a third member having an inner surface defining a cavity, the cavity configured to receive and move the fingers of the first member thereby fixing the first member to the second member,
   wherein the first member includes a first thread form and the third member includes a second thread form, the thread forms being engageable to fix the first member with the second member.

2. A surgical instrument as recited in claim 1, wherein the first member is removably fixed with the second member.

3. A surgical instrument as recited in claim 1, wherein the fingers are circumferentially disposed about the distal end of the first member.

4. A surgical instrument as recited in claim 1, wherein the fingers are circumferentially disposed about the distal end and equidistantly spaced apart from one another.

5. A surgical instrument as recited in claim 1, wherein each of the fingers extends from the distal end of the first member in a cantilevered configuration.

6. A surgical instrument as recited in claim 1, wherein the fingers are each tapered in a distal to proximal direction along a longitudinal axis of the first member such that the fingers jointly define a conical configuration.

7. A surgical instrument as recited in claim 1, wherein the fingers taper to an increased diameter of the first member in a proximal to distal direction along a longitudinal axis of the first member.

8. A surgical instrument as recited in claim 1, wherein the fingers are movable relative to the first member.

9. A surgical instrument as recited in claim 1, wherein the fingers are movable between a first configuration such that the proximal end of the second member slidably engages the inner surface and a second configuration such that the proximal end of the second member is fixed with the inner surface.

10. A surgical instrument as recited in claim 1, wherein the third member includes an outer surface that has a plurality of spaced apart recesses configured to facilitate gripping of the third member.

11. A surgical instrument as recited in claim 1, wherein the members are movable between a first configuration such that the proximal end of the second member slidably engages the inner surface and a second configuration such that the third member engages an outer surface of the fingers to move the fingers into a fixed engagement with the proximal end of the second member.

12. A surgical instrument as recited in claim 1, wherein the cavity comprises a first opening in a proximal end of the third member and a second opening in a distal end of the third member, the fingers being configured to be positioned within the second opening when the first member is disposed in the cavity such that the proximal end of the first member extends through the first opening.

13. A surgical driver comprising:
   a monolithic first member extending between a proximal end and a distal end, the distal end including a plurality of cantilevered fingers extending radially outward in a tapered configuration, the fingers each including an inner surface such that the inner surfaces of the fingers jointly define a cavity;
   a second member extending between a proximal end and a distal end configured for engaging a bone fastener, the proximal end of the second member having a bit configuration defined by a plurality of substantially planar side surfaces, the proximal end of the second member being configured to be received within the cavity such that the side surfaces engage the inner surfaces to prevent rotation of the second member relative to the first member; and
   a third member having an inner surface defining a cavity, the cavity configured to receive the first member, wherein the members are movable between a first configuration such that the proximal end of the second member slidably engages the inner surface and a second configuration such that the third member engages an outer surface of the fingers to move the fingers into engagement with the proximal end of the second member to dispose the members in a locked orientation, and wherein the first member includes a first thread form and the third member includes a second thread form, the thread forms being engageable to fix the first member with the second member.

14. A surgical driver as recited in claim 13, wherein the members are disengageable from the locked orientation.

15. A surgical driver as recited in claim 13, wherein the fingers are movable relative to the first member.

16. A surgical driver as recited in claim 13, wherein the fingers taper to an increased diameter of the first member in a proximal to distal direction.

17. A surgical driver as recited in claim 13, wherein the third member includes an outer surface that has a gripping surface.

18. A surgical driver comprising:

a monolithic collet extending between a proximal end and a distal end, the collet including an outer surface having a first thread form, the distal end including a plurality of cantilevered fingers extending radially outward in a tapered configuration and being spaced apart, the fingers each including an inner surface such that the inner surfaces of the fingers jointly define a socket;

a shaft extending between a proximal end and a distal end configured for engaging a bone fastener, the proximal end including a bit having a plurality of substantially planar side surfaces configured to be received within the socket such that the side surfaces engage the inner surfaces to prevent rotation of the shaft relative to the collet; and a handle having an inner surface defining a cavity configured to receive the collet and a second thread form configured for engagement with the first thread form, wherein the bit is slidably engageable with the inner surface in a first configuration and the third member engages an outer surface of the fingers to move the inner surface into fixation with the bit such that the shaft is disposed in a disengageable locking orientation with the collet, and wherein the collet includes a first thread form and the handle includes a second thread form, the thread forms being engageable to fix the collet with the shaft.

* * * * *

UNITED STATES PATENT AND TRADEMARK OFFICE
CERTIFICATE OF CORRECTION

| | | |
|---|---|---|
| PATENT NO. | : 9,119,685 B2 | Page 1 of 1 |
| APPLICATION NO. | : 13/646990 | |
| DATED | : September 1, 2015 | |
| INVENTOR(S) | : Butler et al. | |

It is certified that error appears in the above-identified patent and that said Letters Patent is hereby corrected as shown below:

In the Claims

In Column 11, Line 60, in Claim 1, delete "within in" and insert -- within --, therefor.

Signed and Sealed this
Sixteenth Day of February, 2016

Michelle K. Lee
*Director of the United States Patent and Trademark Office*